United States Patent

Podubrin et al.

(10) Patent No.: US 6,667,043 B1
(45) Date of Patent: Dec. 23, 2003

(54) TECHNICAL DI- AND TRIGLYCERIDE MIXTURES

(75) Inventors: Stefan Podubrin, Muelheim (DE); Achim Ansmann, Erkrath (DE); Rolf Kawa, Monheim (DE); Richard Ridinger, Monheim (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 690 days.

(21) Appl. No.: 09/117,918

(22) PCT Filed: Feb. 1, 1997

(86) PCT No.: PCT/EP97/00434

§ 371 (c)(1), (2), (4) Date: Aug. 10, 1998

(87) PCT Pub. No.: WO97/29170

PCT Pub. Date: Aug. 14, 1997

(30) Foreign Application Priority Data

Feb. 9, 1996 (DE) .......... 196 04 744

(51) Int. Cl.⁷ .......... A61K 6/00; A61K 7/00; A61K 47/00; A01N 25/00
(52) U.S. Cl. .......... 424/401; 426/417; 426/607; 514/786
(58) Field of Search .......... 424/401, 78.03; 514/786; 426/607, 417

(56) References Cited

U.S. PATENT DOCUMENTS

| | | | | |
|---|---|---|---|---|
| 2,988,483 A | * | 6/1961 | Barsky et al. | 426/605 |
| 3,547,828 A | | 12/1970 | Mansfield et al. | 252/351 |
| 3,658,555 A | * | 4/1972 | Menz et al. | |
| 3,707,535 A | | 12/1972 | Lew | 260/210 R |
| 3,772,269 A | | 11/1973 | Lew | 260/210 R |
| 3,839,318 A | | 10/1974 | Mansfield | 260/210 R |
| 4,172,887 A | | 10/1979 | Vanlerberghe et al. | 424/70 |
| 4,349,669 A | | 9/1982 | Klahr et al. | 536/127 |
| 5,213,812 A | | 5/1993 | Ruiz | 424/499 |
| 5,254,331 A | | 10/1993 | Mausner | 424/59 |
| 5,569,467 A | | 10/1996 | Ruiz | 424/489 |

FOREIGN PATENT DOCUMENTS

| | | |
|---|---|---|
| DE | 11 65 574 | 3/1964 |
| DE | 19 43 689 | 3/1970 |
| DE | 20 36 472 | 2/1971 |
| DE | 27 11 470 | 9/1977 |
| DE | 30 01 064 | 7/1981 |
| DE | 20 24 051 | 5/1986 |
| EP | 0 077 167 | 4/1983 |
| FR | 2 252 840 | 8/1975 |
| FR | 2 665 360 | 2/1992 |
| FR | 2 705 232 | 11/1994 |
| GB | 160 840 | 10/1922 |
| GB | 808 634 | 2/1959 |
| GB | 820 269 | 9/1959 |
| GB | 820 270 | 9/1959 |
| GB | 962919 | 7/1964 |
| GB | 1333475 | 10/1973 |
| GB | 1 516 489 | 7/1978 |
| JP | 62-263143 | 11/1987 |
| JP | 04-314790 | 11/1992 |
| JP | 05-320677 | 12/1993 |

OTHER PUBLICATIONS

"Kosmetische Faerbemittel", Farbstoffkommission der Deutschen Forschungsgemeinschaft, Verlag Chemie, Weinheim (1984), pp. 81–106.

Safety Data Sheet, KET JENLUBE 2700 (Jan. 8, 1994).

* cited by examiner

Primary Examiner—Sreeni Padmanabhan
Assistant Examiner—Lauren Q. Wells
(74) Attorney, Agent, or Firm—John E. Drach; Steven J. Trzaska

(57) ABSTRACT

A process for making technical di/triglyceride mixtures involving: (a) providing a vegetable oil; and (b) partially transesterifying the vegetable oil by reacting it with a component selected from the group consisting of a mixture of glycerol and a fatty acid corresponding to formula I:

$$R^1COOH \qquad (I)$$

wherein $R^1CO$ is an acyl group having from 6 to 10 carbon atoms, a mixture of glycerol and a methyl ester of the fatty acid of formula I, and a triglyceride based on the fatty acid of formula I.

12 Claims, No Drawings

TECHNICAL DI- AND TRIGLYCERIDE MIXTURES

This Application is a 371 of PCT/EP97/00434, filed Feb. 1, 1997.

BACKGROUND OF THE INVENTION

This invention relates to technical di-/triglyceride mixtures which are obtained by partial transesterification of vegetable oils with methyl esters, to a process for their production and to their use as oils for the production of cosmetic and/or pharmaceutical formulations.

DISCUSSION OF RELATED ART

The production of cosmetic and/or pharmaceutical preparations generally requires a hydrophilic phase and a hydrophobic phase. A broad range of oils is available to the expert for formulating such preparations. For reasons of cost, however, inexpensive paraffin oil fractions are frequently used. Although paraffin oil fractions exhibit favorable viscosity behavior and are also suitable for dissolving numerous active ingredients, they do not fit into the commercially desirable concept of a "green" formulation, i.e. a formulation based predominantly on natural, preferably vegetable, raw materials. Possible alternatives are, of course, such raw materials as, for example, glycerol tricaprylate. Unfortunately, raw materials of this type have to be produced by a special and technically elaborate synthesis from glycerol and caprylic acid and, for this reason, are about three times as expensive as paraffin oil fractions.

Accordingly, the complex problem addressed by the present invention was to provide new oils which could be produced at minimum cost from vegetable raw materials and which would therefore represent an economically acceptable alternative to paraffin oil fractions. At the same time, the oils according to the invention would meet a complex requirement profile, i.e. would be light-colored and odorless, would show adequate stability in storage and at low temperatures and, in particular, would have a cloud point below +6° C.

DESCRIPTION OF THE INVENTION

The present invention relates to technical di-/triglyceride mixtures which are obtained by partly transesterifying refined, predominantly saturated vegetable oils with (a) a mixture of glycerol and fatty acids corresponding to formula (I):

$$R^1COOH \qquad (I)$$

in which $R^1CO$ is an acyl group containing 6 to 10 carbon atoms, or methyl esters thereof or (b) triglycerides based on the fatty acids corresponding to formula (I).

It has surprisingly been found that, by partly transesterifying simple refined vegetable oils with short-chain fatty compounds, the titer can be reduced to such an extent that the products not only become liquid at room temperature, they also exhibit the required stability in storage at low temperatures.

The present invention also relates to a process for the production of technical di-/triglyceride mixtures in which refined predominantly saturated vegetable oils are partly transesterified with (a) a mixture of glycerol and fatty acids corresponding to formula (I):

$$R^1COOH \qquad (I)$$

in which $R^1CO$ is an acyl group containing 6 to 10 carbon atoms, or methyl esters thereof or (b) triglycerides based on the fatty acids corresponding to formula (I).

Vegetable Oils

Suitable starting materials are predominantly saturated vegetable oils which have an iodine value of 0.5 to 50. The vegetable oils are derived from fatty acids which may contain from 6 to 22 carbon atoms, although the focal point of the carbon chain distribution is in the range from 12 to 18 carbon atoms. This means that at least 80% of the fatty acids present in the vegetable oils contain from 12 to 22 and preferably from 12 to 18 carbon atoms. Typical examples are palm oil, palm kernel oil, babassu oil and/or coconut oil which are also particularly preferred. Vegetable oils which may be used after hydrogenation, i.e. after reduction of their iodine value, are olive oil, sunflower oil, rapeseed oil, peanut oil, cottonseed oil, tea seed oil chaulmoogra oil, coriander oil, linseed oil and meadowfoam oil.

Fatty Acids, Fatty Acid Methyl Esters and Triglycerides

Fatty acids suitable for partial transesterification in the presence of glycerol are caproic acid, capric acid and—in particular—caprylic acid. Instead of the fatty acids, the corresponding methyl esters may also be used. In one variant of the invention, the partial transesterification may also be directly carried out with triglycerides based on the fatty acids mentioned. Accordingly, there is no need to use glycerol.

Transesterification

In the reaction of the vegetable oils with the fatty compounds mentioned above and, optionally, the glycerol, various reactions take place alongside one another and lead to a complex mixture of diglycerides and triglycerides. In the case of the methyl ester for example, the vegetable oils undergo partial transesterification, i.e. the relatively long-chain fatty acids of the vegetable oil are at least partly replaced by the relatively short-chain fatty acids of the methyl ester. The relatively long-chain fatty acids released may, then in turn form esters with the free glycerol. Transesterification of the short-chain methyl ester with the glycerol is also possible under these conditions.

The complex reaction, which in the interests of simplicity is referred to herein as "partial transesterification", normally takes place at temperatures of 140 to 250° C. and preferably at temperatures of 210 to 230° C. Catalysts suitable for this purpose are known substances such as, for example, zinc soaps, tin grindings, tin oxides, titanic acid esters, alkali metal hydroxides, carbonates or alcoholates and the like which are used in quantities of 0.05 to 1% by weight and preferably in quantities of 0.1 to 0.5% by weight, based on the starting materials. It is advisable to remove the methanol released during the reaction continuously from the reaction equilibrium and to neutralize the catalyst on completion of the reaction, for example by addition of bleaching earth, in order not to catalyze any back-reactions during the removal of unreacted methyl ester by distillation.

It has also proved to be of advantage to use the vegetable oils, the fatty acids or methyl esters and the glycerol in a molar ratio of 1:(2.5 to 3.5):(1.0 to 2.0), molar ratios of 1:(3.0 to 3.4):(1.3 to 1.6) being particularly preferred because an almost complete conversion is obtained under these conditions. If triglycerides are used, the ratio is calculated in the same way, but must of course be based on the number of acyl groups. As already mentioned, there is no need in these cases to use glycerol, although glycerol may be used in small amounts. The products obtained in every case have a percentage monoglyceride content below 5% by weight and are characterized by a ratio by weight of diglycerides to triglycerides of 1:3 to 1:6. Di-/triglyceride mixtures such as these are distinguished by optimal performance properties.

If necessary, the di-/triglyceride mixtures obtained after the transesterification may be subjected in known manner to deodorization. To this end, the oils are normally treated with hot steam either continuously in a falling-film column or discontinuously in a boiler, so that the steam-volatile odor carriers (for example short-chain aldehydes or ketones) are almost quantitatively removed.

Commercial Applications

The technical di-/triglyceride mixtures according to the invention are liquid at room temperature, have a cold cloud point below +6° C. and are light-colored, odorless and stable in storage. Accordingly, the present invention also relates to their use as oils for the production of cosmetic and/or pharmaceutical formulations in which they may be present in quantities of 1 to 95% by weight and preferably in quantities of 15 to 50% by weight.

Typical examples of formulations in which the new oils may be used are skin-care products such as, for example, day cremes, night cremes, skin-care cremes, nourishing cremes, body lotions, sunscreens, emollients and the like which contain additional oils, surfactants, emulsifiers, superfatting agents, stabilizers, waxes, consistency regulators, thickeners, cationic polymers, silicone compounds, biogenic agents, antidandruff agents, film formers, preservatives, hydrotropes, solubilizers, UV adsorbers, dyes and fragrances as further auxiliaries and additives.

Suitable additional oils are, for example, Guerbet alcohols based on fatty alcohols containing 6 to 18 carbon atoms and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer triol) and/or Guerbet alcohols, triglycerides based on $C_{6-10}$ fatty acids, esters of $C_{6-22}$ fatty alcohols and/or Guerbet alcohols with aromatic carboxylic acids, particularly benzoic acid, vegetable oils, branched primary alcohols, substituted cyclohexanes, Guerbet carbonates, dialkyl ethers, silicone oils and/or aliphatic or naphthenic hydrocarbons.

Typical examples of suitable surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, ether carboxylic acids, alkyl oligoglucosides, fatty acid glucamides, alkyl amidobetaines and/or protein fatty acid condensates.

Suitable emulsifiers are, for example, nonionic surfactants from at least one of the following groups:

(b1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms;

(b2) $C_{12/18}$ fatty acid monoesters and diesters of adducts of 1 to 30 moles of ethylene oxide with glycerol;

(b3) glycerol monoesters and diesters and sorbitan monoesters and diesters of saturated and unsaturated fatty acids containing 6 to 22 carbon atoms and ethylene oxide adducts thereof;

(b4) alkyl mono- and oligoglycosides containing 8 to 22 carbon atoms in the alkyl group and ethoxylated analogs thereof;

(b5) adducts of 15 to 60 moles of ethylene oxide with castor oil and/or hydrogenated castor oil;

(b6) polyol esters and, in particular, polyglycerol esters such as, for example, polyglycerol polyricinoleate or polyglycerol poly-12-hydroxystearate. Mixtures of compounds from several of these classes are also suitable;

(b7) adducts of 2 to 15 moles of ethylene oxide with castor oil and/or hydrogenated castor oil;

(b8) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(b9) trialkyl phosphates;

(b10) wool wax alcohols;

(b11) polysiloxane/polyalkyl polyether copolymers and corresponding derivatives;

(b12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol, and (b13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use as surfactants are known, for example, from U.S. Pat. No. 3,839,318, U.S. Pat. No. 3,707,535, U.S. Pat. No. 3,547,828, DE-OS 19 43 689, DE-OS 20 36 472 and DE-A1 30 01 064 and EP-A 0 077 167. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3- carboxymethyl3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, especially methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers. The consistency regulators mainly used are fatty alcohols containing 12 to 22 and preferably 16 to 18 carbon atoms. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives, cationic starch, copolymers of diallyl ammonium salts and acrylamides, quatemized vinyl pyrrolidonelvinyl imidazole polymers such as, for example, Luviquat® (BASF AG, Ludwigshafen, FRG), condensation products of polyglycols and amines, quaternized collagen polypeptides such as, for example, Lauryldimonium Hydroxypropyl Hydrolyzed Collagen (Lame quat®L, Grünau GmbH), quatemized wheat polypeptides, polyethyleneimine, cationic silicone polymers such as, for example, Amidomethicone or Dow Corning, Dow Corning Co., USA, copolymers of adipic acid and dimethylamino-hydroxypropyl diethylenetriamine (Cartaretine®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkylene, for example dibromobutane, with bis-dialkylamines, for example bis-dimethylamino-1,3-propane, cationic guar gum such as, for example, Jaguar®CBS, Jaguar®C-17, Jaguar®C-16 of Celanese, USA, quaternized ammonium salt polymers such as, for example, Mirapol®A-15, Mirapol®AD-1, Mirapol®AZ-1 of Miranol, USA.

Suitable silicone compounds are, for example, dimethyl polysiloxanes, methylphenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, paraffin wax or microwaxes, optionally in combination with hydrophilic waxes, for example cetyl stearyl alcohol, or partial glycerides. The pearlescing waxes used may be, in particular, mono- and difatty acid esters of polyalkylene glcols, partial glycerides of esters of fatty alcohols with polybasic carboxylic acids or hydroxy-carboxylic acids. Metal salts of fatty acids such as, for example, magnesium, aluminium and/or zinc stearate may be used as stabilizers. In the context of the invention, biogenic agents are, for example, bisabolol, allantoin, phytantriol, panthenol, AHA acids, plant extracts and vitamin complexes. Climbazol, octopirox and zinc pyrethion may be used as antidandruff agents. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. In addition, hydrotropes such as, for example, ethanol, isopropyl alcohol, propylene glycol or glucose may be used to improve flow behavior. Suitable preservatives are, for example, phenoxyethanol, formaldehyde solution, parabens, pentanediol or sorbic acid. The dyes used may be selected from any of the substances which are approved and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total content of auxiliaries and additives may be from 1 to 50% by weight and is preferably from 5 to 40% by weight, based on the formulation. The formulations may be produced by standard cold or hot processes and are preferably produced by the phase inversion temperature method.

EXAMPLES

Example 1

In a 2 liter distillation apparatus, a mixture of 657 g (1 mole) of refined coconut oil, 665 g (4.2 moles) of caprylic acid methyl ester, 129 g (1.4 moles) of glycerol and 1.5 g of tin(II) oxide—corresponding to 0.1% by weight, based on the starting materials—was heated under reflux for 8 h to 230° C. and the methanol released was continuously removed from the reaction equilibrium. The unreacted methyl ester was then distilled off and the catalyst was neutralized by addition of 2 g of bleaching earth. The resulting oil was then deodorized by treatment with hot steam. 1100 g of a light yellow odorless oil containing 0.8% by weight of monoglycerides, 22.0% by weight of diglycerides and 77.2% by weight of triglycerides were obtained.

Example 2

673 g (1 mole) of refined palm kernel oil, 679 g (4.3 moles) of caprylic acid methyl ester, 132 g (1.4 moles) of glycerol and 1.5 9 of tin(II) oxide—corresponding to 0.1% by weight, based on the starting materials—were heated under reflux for 6 h to 220° C. as in Example 1. 1080 g of a light yellow odorless oil containing 2.2% by weight of monoglycerides, 20.2% by weight of diglycerides and 75.9% by weight of triglycerides were obtained.

Example 3

657 g (1 mole) of refined coconut oil, 499 g (3.2 moles) of head-fractionated fatty acid (C chain: $C_{6-10}$), 129 g (1.4 moles) of glycerol and 1.5 g of tin(II) oxide—corresponding to 0.1% by weight, based on the starting materials—were heated for 6 h to 220° C. as in Example 1, the water of reaction being continuously removed. 1070 g of a light yellow odorless oil containing 1.8% by weight of monoglycerides, 20.2% by weight of diglycerides and 78.0% by weight of triglycerides were obtained after refining and deodorization.

Example 4

657 g (1 mole) of refined coconut oil, 502 g (1.1 mole) of glycerol tricaprylate, 28 g (0.3 mole) of glycerol and 1.5 g of tin(II) oxide—corresponding to 0.1 % by weight, based on the starting materials—were heated for 8 h to 220° C. as in Example 1. 1030 g of a light yellow odorless oil containing 0.9% by weight of monoglycerides, 23.1% by weight of diglycerides and 76.0% by weight of triglycerides were obtained after refining and deodorization

Example 5

657 g (1 mole) of refined coconut oil, 456 g (1 mole) of glycerol tricaprylate and 1.1 g of sodium methylate—corresponding to 0.1% by weight, based on the starting materials—were heated with stirring in vacuo for 6 h to 210° C. 980 g of a light yellow odorless oil were obtained after refining and deodorization.

What is claim is:

1. A process for making di-/triglyceride mixtures comprising:

(a) providing a vegetable oil having an iodine value of from 0.5 to 50; and (b) partially transesterifying the vegetable oil by reacting it with a transesterifying component selected from the group consisting of a mixture of glycerol and a fatty acid corresponding to formula I:

$$R^1COOH \qquad (I)$$

wherein $R^1CO$ is an acyl group having from 6 to 10 carbon atoms, a mixture of glycerol and a methyl ester of the fatty acid of formula I, and triglycerides derived from the fatty acid of formula I in a molar ratio of vegetable oil to transesterifying component of 1:(2.5 to 3.5) so that the di-/triglyceride mixture has a ratio by weight of diglycerides to triglycerides of from 1:3 to 1:6, a monoglyceride content of less than 5% by weight, and a cloud point below +6° C.

2. The process of claim 1 wherein the fatty acid is selected from the group consisting of caproic acid, capric acid, capric acid methyl ester and caprylic acid.

3. The process of claim 1 wherein the reaction is conducted at a temperature of from 140 to 250° C.

4. The process of claim 1 wherein the vegetable oil, fatty acid and glycerol are combined in a molar ratio of 1:(2.5 to 3.5):(1.0 to 2.0).

5. The process of claim 1 wherein the vegetable oil is selected from the group consisting of palm oil, palm kernel oil, babassu oil, coconut oil and mixtures thereof.

6. The product of the process of claim 1.

7. The product of the process of claim 2.

8. The product of the process of claim 3.

9. The product of the process of claim 4.

10. The product of the process of claim 5.

11. A cosmetic composition containing from 1 to 95% by weight, based on the weight of the composition, of the di-/triglyceride mixture of claim 1.

12. A pharmaceutical composition containing from 1 to 95% by weight, based on the weight of the composition, of the di-/triglyceride mixture of claim 1.

\* \* \* \* \*